US010022543B2

(12) United States Patent
Olson (10) Patent No.: US 10,022,543 B2
(45) Date of Patent: Jul. 17, 2018

(54) CELL STIMULATION USING QUANTUM DOTS

(75) Inventor: Jefferey Olson, Cherry Hills, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 322 days.

(21) Appl. No.: 13/144,277

(22) PCT Filed: Jan. 12, 2010

(86) PCT No.: PCT/US2010/020815
§ 371 (c)(1),
(2), (4) Date: Jul. 12, 2011

(87) PCT Pub. No.: WO2010/083170
PCT Pub. Date: Jul. 22, 2010

(65) Prior Publication Data
US 2011/0270153 A1    Nov. 3, 2011

Related U.S. Application Data (60) Provisional application No. 61/144,155, filed on Jan. 13, 2009.

(51) Int. Cl.
| | |
|---|---|
| *A61M 37/00* | (2006.01) |
| *A61N 1/36* | (2006.01) |
| *A61N 1/378* | (2006.01) |
| *A61N 5/06* | (2006.01) |
| *B82Y 15/00* | (2011.01) |
| *B82Y 30/00* | (2011.01) |
| *C12N 13/00* | (2006.01) |

(52) U.S. Cl.
CPC ........ *A61N 1/36046* (2013.01); *A61N 1/3787* (2013.01); *A61N 5/0603* (2013.01); *A61N 5/0622* (2013.01); *B82Y 15/00* (2013.01); *B82Y 30/00* (2013.01); *A61N 2005/0659* (2013.01)

(58) Field of Classification Search
CPC .................... A61N 1/36046; A61N 1/3787
USPC .......................................................... 506/9
See application file for complete search history.

(56) References Cited

U.S. PATENT DOCUMENTS

| | | | | |
|---|---|---|---|---|
| 6,682,523 | B2 * | 1/2004 | Shadduck | ............ 606/6 |
| 7,139,612 | B2 | 11/2006 | Chow et al. | |
| 7,531,503 | B2 * | 5/2009 | Atala et al. | ...... 514/1.1 |
| 8,388,668 | B2 | 3/2013 | Peyman | |
| 8,409,263 | B2 | 4/2013 | Peyman | |
| 8,460,351 | B2 | 6/2013 | Peyman | |
| 8,725,266 | B2 | 5/2014 | Olson | |
| 2002/0147442 | A1 | 10/2002 | Shadduck | |
| 2003/0022374 | A1 * | 1/2003 | Greenbaum | ...... C07K 14/705 435/455 |
| 2003/0022831 | A1 | 1/2003 | Rothbard et al. | |
| 2005/0017176 | A1 * | 1/2005 | Koch | ............ B82Y 10/00 250/338.4 |
| 2005/0090874 | A1 | 4/2005 | Wu et al. | |
| 2005/0136258 | A1 | 6/2005 | Nie et al. | |
| 2006/0129210 | A1 | 6/2006 | Cantin et al. | |
| 2006/0204441 | A1 | 9/2006 | Atala et al. | |
| 2006/0287660 | A1 | 12/2006 | Syed et al. | |
| 2007/0028928 | A1 | 2/2007 | Peyman | |
| 2008/0220982 | A1 | 9/2008 | Vu | |
| 2008/0221645 | A1 | 9/2008 | Kennedy et al. | |
| 2008/0241071 | A1 | 10/2008 | West et al. | |
| 2010/0185260 | A1 | 7/2010 | Olson | |

FOREIGN PATENT DOCUMENTS

| | | |
|---|---|---|
| WO | 2004004927 | 1/2004 |
| WO | 2005018681 | 3/2005 |
| WO | 2005041747 | 5/2005 |

OTHER PUBLICATIONS

Todd C. Pappas, W. M. Shan Wickramanyake, Edward Jan, Massoud Motamedi, Malcolm Brodwick, and Nicholas A. Kotov in "Nanosclae Engineering of a Cellular Interface with Semiconductor Nanoparticle Films for Photoelectric Stimulation of Neurons" (Nano Letters, vol. 7, No. 2, pp. 513-519, published in 2007).*
U.S. Appl. No. 12/528,832, filed Jul. 2011, Olson et al.*
httpwww.ncbi.nlm.nih.govpubmedhealthPMH0001740; accessed Dec. 2, 2012.*
Pappas et al., "Nanoscale Engineering of a Cellular Interface with Semiconductor Nanoparticle Films for Photoelectric Stimulation of Neurons", Nano Letters, vol. 7, No. 2, p. 513-519 (2007).*
Hirsch et al., "Nanoshell-mediated near-infrared thermal therapy of tumors under magnetic resonance guidance", Proceedings of the National Academy of Sciences, vol. 100, No. 23., p. 13549-13554 (2003).*
Choi et al., "Quantum dot-induced cell death involves Fas upregulation and lipid peroxidation in human neuroblastoma cells", Journal of Nanobiotechnology, vol. 5, p. 1-13 (2007).*
Evident Technologies Quantum Dot Specifications Sheet, 2006, pp. 1-6.*
Final Rejection in U.S. Appl. No. 12/528,832 dated Jan. 9, 2014.
Non-final rejection dated Oct. 11, 2013 in Canadian Application No. 2,716,991.
Non-final Rejection in U.S. Appl. No. 12/528,832 dated Sep. 6, 2013.
Advisory Action in U.S. Appl. No. 12/528,832 dated Jul. 23, 2013.
Final Rejection in U.S. Appl. No. 12/528,832 dated May 17, 2013.
Office Action dated Mar. 9, 2012 in Canadian Application No. 2,716,991.
Office Action dated Jan. 17, 2013 in Canadian Application No. 2,716,991.
First Examination Report dated Sep. 10, 2012 for European Patent Application No. 08 730 992.8-2112.

(Continued)

*Primary Examiner* — Karla A Dines
(74) *Attorney, Agent, or Firm* — Snell & Wilmer L.L.P.

(57) ABSTRACT

The present invention provides methods for stimulating cells using quantum dots. In addition, the present invention provides methods for treating a variety of clinical conditions using stimulation of quantum dots to induce cell stimulation and/or function.

4 Claims, 3 Drawing Sheets

(56) References Cited

OTHER PUBLICATIONS

Result of Consultation dated Oct. 4, 2012 for European Patent Application No. 08 730 992.8-2112.
Evident Technologies, EviTag Luminescent Labels, Quantum Dot EviTags, "Unique Optical Properties and Biological, Flexible Surfaces to Enable New Life Science Research" dated Mar. 2005, Specification Sheet.
Non-final Rejection in U.S. Appl. No. 12/528,832 dated Dec. 18, 2012.
Goldman, E. et al., "Avidin: A Natural Bridge for Quantum Dot-Antibody Conjugates," JACS, 2002, 124(22), pp. 6378-6382.
Notification Concerning Transmittal of International Preliminary Report on Patentability dated Sep. 11, 2009.
Notification of Transmittal of the International Search Report and the Written Opinion of the International Search Authority, or the Declaration dated Aug. 20, 2008.
EP; Extended Search Report and Preliminary Opinion dated Nov. 11, 2011 in Application No. 08730992.8.
Akerman et al., "Nanocrystal Targeting in Vivo," PNAS USA, 2002, 99, pp. 12617-12621.
Written Opinion of the International Searching Authority concerning PCT/US08/55332 dated Aug. 20, 2008.
Office Action dated Mar. 28, 2016 in U.S. Appl. No. 14/827,970.
Communication Pursuant to Article 94(3) EPC dated Feb. 1, 2016 in European Application No. 08730992.8.
B.M. Lingerfelt, et al., "Preparation of Quantum Dot—Biotin Conjugates and Their Use in Immunochromatography Assays," Analytical Chemistry, vol. 75, No. 16, dated Aug. 15, 2003, pp. 4043-4049.
X. Michalet, et al., "Quantum Dots for Live Cells, in Vivo Imaging and Diagnostics," Science, 307 (1509), dated at least as early as Sep. 13, 2005, pp. 1-16.
C. Xu, et al., "A self-assembled quantum dot probe for detecting Beta-lactamase activity," Biochemical and Biophysical Research Communications, 344, dated Apr. 19, 2006, pp. 931-935.
Notice of Allowance dated Mar. 7, 2014 in U.S. Appl. No. 12/527,932.
International Search Report and Written Opinion dated Sep. 6, 2010 in Application No. PCT/US2010/020815.
International Preliminary Report on Patentability dated Jul. 19, 2011 in Application No. PCT/US2010/020815.
Office action received in Canadian Patent App. No. 2,716,991 dated Aug. 1, 2014.
Examination Report in EP Application No. 08730992.8 dated Jun. 4, 2014.
Office Action dated May 22, 2015 in U.S. Appl. No. 14/249,079.
Notice of Allowance dated Apr. 9, 2015 in Canadian Patent App. No. 2,716,991 dated Aug. 1, 2014.
Notice of Allowance dated Aug. 18, 2015 in U.S. Appl. No. 14/249,079.
Final Office Action dated Oct. 24, 2016 in U.S. Appl. No. 14/827,970.
Communication under Rule 71(3) EPC dated Apr. 5, 2017 in European Application No. 08730992.8.

\* cited by examiner

CELL STIMULATION USING QUANTUM DOTS

CROSS-REFERENCE TO RELATED APPLICATIONS

This application is a U.S. national phase filing under 35 U.S.C. § 371 of PCT/US2010/20815, filed on Jan. 12, 2010, which claims priority from U.S. Provisional Patent Application No. 61/144,155, filed on Jan. 13, 2009, both of which are incorporated herein by reference in their entireties.

FIELD OF THE INVENTION

The present invention relates to use of quantum dots to induce cell stimulation or cell function.

BACKGROUND OF THE INVENTION

Many people suffer from various forms of neural cell damage or impaired neural cell function. Clinical conditions associated with neural cell damage or impaired neural cell function include, but are not limited to, retinal damage (such as retinitis pigmentosa, retinal detachment, diabetic retinopathy, and macular degeneration), optic neuropathy, glaucoma, stroke, spinal cord injury, peripheral nerve injury, demylinating disease (such as multiple sclerosis), and central nervous system injury secondary to ischemia, compression, injury, infection, elevated incranial pressure, congenital and hereditary genetic disease, metabolic derangement, tumors, toxic neuropathy and encephalopathy, lysosomal storage diseases, mitochondrial diseases, neurological sequelae of systemic diseases such as chronic arterial hypertension, diabetes, HIV infection, systemic lupus, coagulation disorders, Parkinsons disease, Alzheimers disease, and prion disease. Retinal damage or impaired retinal function can lead to diminished sight and blindness. And, as the age of the general population increases, the number of people suffering from diminished sight due to these causes increases.

Since many cells such as neurons, including retina, are stimulated via electrical signals, it has also been known that functions of these cells can be restored by providing an appropriate electrical stimulation. In fact, several devices have been developed to attempt to restore vision loss due to retinal damage. For example, photovoltaic devices, which are attached to a portion of a retina, have been developed to stimulate rods and cones within the retina. Although such devices may provide some stimulation, the devices suffer from several drawbacks. In particular, the devices are relatively large (e.g., on the order of square millimeters). As a result, when placed on a retina, the devices block significant portions of light that would otherwise reach rods and cones located behind the devices. Another problem associated with these devices is that they are placed on a surface of the retina, which is delicate; thus, the retina surface may tear or otherwise become damaged when the devices are attached to the retina.

Other silicon-chip based devices that are implanted sub-retinally have also been developed to attempt to improve vision in those suffering from retinal damage. Mild improvement of electrical response to light has been observed using these devices. However, several problems have also been observed. Specifically, because the devices are relatively large, once the devices are attached to the retina, oxygen is blocked from reaching cells adjacent to or proximate the devices. In addition, implantation of the devices is thought to further damage the retinal tissue.

Accordingly, there is a need for a method for electrically stimulating cells using a significantly smaller device and without causing further damage to the cells.

SUMMARY OF THE INVENTION

Some aspects of the invention provide methods for electrically stimulating cells using a composition comprising a quantum dot. Such methods typically comprise irradiating the composition with electromagnetic radiation comprising infrared radiation, which is absorbed by the quantum dot. The resulting quantum dot produces an electrical energy that is capable of stimulating the cell. The composition is located sufficiently proximal to the cell such that the produced electrical energy by the quantum dot causes the cell to be stimulated. Further, the quantum dots may in some instances be internalized within the cell and stimulate internally.

In some embodiments, the produced electrical energy comprises fluorescence, a photovoltaic response, or a combination thereof. In some particular instances, the produced electrical energy comprises a photovoltaic response.

In other embodiments, the cell is retinal cell. Yet in other embodiments, the cell is a neural cell. Within these embodiments, in some instances the neural cell is peripheral neural cell. Yet in other instances the neural cell is central neural cell.

Still in other embodiments, the composition further comprises a bio-compatible protein, PEG lipids or other suitable material, biofunctional material, formed of, for example, biotin, streptavadin, adhesion proteins, vitamins, organic and inorganic compounds, carbohydrates, aptamers, amino acids, lipids, hyaluronic acid, or other suitable proteins. Within these embodiments, in some instances the bio-compatible protein comprises an adhesion protein. Such proteins include, but are not limited to, individual amino acids, small peptides, antibodies including human, animal, humanized, monoclonal, and chimeric antibodies used to target various cells and cellular structures, as well as the various classes of antibodies such as IgG, IgM, IgA, IgM, and IgD.

Still other aspects of the invention provide methods for treating a clinical condition associated with an impaired neural cell function. Typically, such methods include
   placing a composition comprising a quantum dot within a location sufficient to cause the neural cell function to be stimulated by electrical energy produced by the quantum dot; and
   irradiating the composition with electromagnetic radiation comprising a wavelength that is absorbed by the quantum dot and is reemitted as an electrical energy that sufficiently stimulates the neural cell function to treat the clinical condition.

Typically, the quantum dot is an infrared quantum dot. In such instances electromagnetic radiation used to irradiate the composition comprises infrared radiation.

In some embodiments, the electrical energy produced by the quantum dot comprises fluorescence, a photovoltaic response by the quantum dot, or a combination thereof.

Yet in other embodiments, the clinical condition comprises stroke, spinal cord injury, peripheral nerve injury, demylinating disease, or a combination thereof.

Still in other embodiments, the clinical condition comprises multiple sclerosis, ameliorated lateral sclerosis, central nervous system injury secondary to ischemia, compression injury, infection, elevated incranial pressure, congenital and hereditary genetic disease, metabolic derangement, tumors, toxic neuropathy and/or encephalopathy, lysosomal storage diseases, mitochondrial diseases, neurological sequelae of systemic diseases such as chronic arterial hypertension, diabetes, HIV infection, systemic lupus, coagulation disorders, Parkinsons disease, Alzheimers disease, prion disease, or a combination thereof.

BRIEF DESCRIPTION OF THE INVENTION

DETAILED DESCRIPTION OF THE INVENTION

Many cells such as neurons and retina are stimulated via electrical signals. Impaired cell function or lack of means for stimulating such cells results in a variety of clinical conditions. Exemplary clinical conditions associated with lack of proper electrical stimulation of a cell include, but are not limited to, retinal damage (such as retinitis pigmentosa, retinal detachment, trauma, diabetic retinopathy, and macular degeneration), optic neuropathy, glaucoma, stroke, spinal cord injury, peripheral nerve injury, demylinating disease (such as multiple sclerosis), and central nervous system injury secondary to ischemia, compression, injury, infection, elevated incranial pressure, congenital and hereditary genetic disease, metabolic derangement, tumors, toxic neuropathy and encephalopathy, lysosomal storage diseases, mitochondrial diseases, neurological sequelae of systemic diseases such as chronic arterial hypertension, diabetes, HIV infection, systemic lupus, coagulation disorders, Parkinsons disease, Alzheimers disease, and prion disease. As an example, millions of Americans suffer from retinal disease. For these people, each day brings a further diminution of their vision. Despite recent technological and pharmacologic advances in medicine, the number of people losing sight continues to increase, due in large part to blinding diseases such as macular degeneration, diabetic retinopathy, and hereditary retinal degenerations. Often the vision loss is irreversible—at least by conventional means.

Vision loss is one of the most feared disabilities, and is affecting more Americans than ever before. Alarmingly, the number of people with visual impairment in this country is expected to double over the next thirty years.

Age-related macular degeneration (AMD), diabetic retinopathy and retinitis pigmentosa are the leading causes of blindness in the United States. An estimated 27 million Americans are affected by one of these conditions. Unfortunately, patients considered legally blind often continue to lose vision over time despite the best available treatments. This has profound social, psychological, and economic impact for both the individual and society at large. It is estimated that the economic burden at a Federal level, from benefits and lost taxable income, exceeds $4 billion annually.

Loss of vision from retinal disorders generally occurs secondary to degeneration or damage to retinal photoreceptors. Attempts to transplant the retina have met with limited success, largely due to the inherent intricacy of the biological wiring involved. There are over 120 million rods and 6 million cones, which upon exposure to light generate an action potential. This signal then travels through a complex interconnection of bipolar and amacrine cells which process visual information before converging into one million ganglion cells and traveling to the central nervous system via the optic nerve. The retina, like most mammalian nervous tissue, has a limited capacity to regenerate once damaged. It can, however, respond to external or artificial stimulation. Since most of these cells respond to electrical stimulation, functions of these cells can be induced by providing an appropriate electrical stimulation.

Reversal of blinding disorders is an area of intense investigation, and numerous groups around the world are actively involved in "artificial vision" projects. There are two basic approaches under investigation: implants which are placed on the surface of the retina (epiretinal) and implants beneath the retina (subretinal).

Epiretinal implants have a major limitation in that they are positioned in front of the retina, and actually prevent light from reaching the photoreceptors. The implant itself requires a high degree of complexity in order to emulate the complex neural circuit it is designed to bypass.

Subretinal implants are situated beneath the retina. Conventional subretinal implants have a major limitation in that they block the retina from its nutrient source, the choroid, a highly vascularized layer of tissue which rests beneath the avascular photoreceptor layer. Decreased oxygen delivery leads to an increased rate of photoreceptor cell death in the vicinity of the implant.

Another drawback to current projects underway is the fact that both the subretinal and epiretinal implants are large in the relative framework of the human eye, and cause collateral damage to the tissue they are intended to help, leading to minimal or transitory functional improvement in vision. Further, the current artificial retinal projects are plagued by the need for additional external processors, cameras, and other peripheral devices. The more complex the system becomes, the greater the chance for breakdown.

Some aspects of the invention avoid the problems encountered by other artificial vision projects through the use of photoactive nanoparticles deployed on the cellular level, allowing less invasive methods for implantation and significantly minimizing traumatic damage to the retinal photoreceptors. These particles, known as quantum dots ("QDs"), are discrete nanoparticles that have properties similar to bulk semiconductors such that when exposed to electromagnetic energy they in turn emit energy. Quantum dots can be engineered to be sensitive to energy in the infrared region, the visible spectrum, and even ultraviolet range through changes in size and composition. Further, they can be designed to be either photoluminescent or photovoltaic, producing either light or energy, respectively.

Quantum dots are semi-conductor nano-crystals that possess several useful properties such as photoluminescence (PL). Photoluminescence refers to absorption of light by a QD at one wavelength and emission of light at a second wavelength. Usually, the absorbed wavelength is shorter than the emitted wavelength. Such a property is called "down converting". The PL properties of QDs have been used by researchers in a wide variety of areas including the areas of biological studies in a process known as "tagging" where a QD is attached to a specific protein or DNA.

QDs are nano-particulate semiconductors, whose excitons are confined in all three spatial dimensions. As a consequence of this quantum confinement, it is believed that QDs possess properties that lie between those of bulk semiconductors and those of discrete molecules. QDs are unique among advanced materials in that their properties can be readily engineered, providing QDs that comprise the same elements, but which, for instance, can be made to emit electromagnetic (EM) radiation at different wavelengths by changing the size or the relative composition of the QD.

Colloidal semiconductor QDs are typically synthesized from precursor compounds dissolved in solution and is often based on a three component system comprising precursors, organic surfactants, and solvents. In a typical process, on heating a reaction medium to the desired temperature, the precursors chemically transform into monomers. Once the monomers reach a high enough super-saturation level, the QD growth commences via a nucleation process. The temperature during the growth process is one of the factors in determining optimal conditions for the QD growth. Generally, the temperature must be sufficiently high to allow for rearrangement and annealing of the atoms during the synthesis process. However, the temperature should not be too high so as to inhibit crystal growth. An additional factor, which also is often controlled during the QD growth process, is the monomer concentration. The growth process of QD often occurs in two different regimes, those being "focusing" and "defocusing". At high monomer concentrations, the critical size (the size where QDs neither grow nor shrink) is very narrow, resulting in growth of nearly all particles. In this regime, the relative rates of growth favor the growth of smaller particles, which provides "focus" and provides a high degree of mono-dispersity with respect to particle size. The size focusing is considered to be optimal when the monomer concentration is kept such that the average QD size present is always slightly larger than the critical size. When the monomer concentration is depleted during growth, the critical size becomes larger than the average size present, and the distribution "defocuses" as a result of a process known as Ostwald ripening.

There are colloidal methods to produce many different semiconductor binary and ternary QDs. Exemplary QDs produced by colloidal methods include, but are not limited to, cadmium-selenide (CdSe), cadmium-sulfide (CdS), indium-arsenide (InAs), and indium-phosphide (InP) cadmium-tellurium-sulfide (CdTeS). The number of atoms that comprise a QD can range from 100 to 100,000 and the diameter for practical purposes can range from 2 to 20 nm.

Other suitable QD materials include, but are not limited to, Carbon, colloidal gold, germanium, indium arsenide, indium antimonide, gallium arsenide, gallium nitride, Cadmium/Selenium/telluride, Lead, lead oxide, lead sulfide, lead selenide, indium gallium phosphide, silicon, colloidal silver, mercury cadmium telluride, iron, iron oxide, cobalt, graphene, Lanthanum, cerium, strontium carbonate, manganese, manganese oxide, nickel oxide, platinum, lithium, lithium titanate, tantalum, copper, palladium, molybdenum, boron carbide, silicon carbide, titanium carbide, tungsten oxide, Aluminum, niobium, thulium, aluminum nitride, tin, aluminum oxide, tin oxide, antimony, dysprosium, paseodynium, antinmony oxide, erbium, rhenium, barium, ruthenium, beryllium, Samarium, Bismuth oxide, Boron, Gadolinium, boron nitride, vanadium oxide, strontium, Ytterbium, zirconium, diamond (C), Silicon (Si), germanium (Ge), silicon carbide (SiC), silicon-germanium (SiGe), Aluminium antimonide (AlSb), Aluminium arsenide (AlAs), Aluminium nitride (AlN), Aluminium phosphide (AlP), Boron nitride (BN), Boron phosphide (BP), Boron arsenide (BAs), Gallium antimonide (GaSb), Gallium arsenide (GaAs), Gallium nitride (GaN), Gallium phosphide (GaP), Indium antimonide (InSb), Indium arsenide (InAs), Indium nitride (InN), Indium phosphide (InP), Aluminium gallium arsenide (AlGaAs, $Al_xGa_{1-x}As$), Indium gallium arsenide (InGaAs, $In_xGa_{1-x}As$), Indium gallium phosphide (InGaP), Aluminium indium arsenide (AlInAs), Aluminium indium antimonide (AlInSb), Gallium arsenide nitride (GaAsN), Gallium arsenide phosphide (GaAsP), Aluminium gallium nitride (AlGaN), Aluminium gallium phosphide (AlGaP), Indium gallium nitride (InGaN), Indium arsenide antimonide (InAsSb), Indium gallium antimonide (InGaSb), Aluminium gallium indium phosphide (AlGaInP, also InAlGaP, InGaAlP, AlInGaP), Aluminium gallium arsenide phosphide (AlGaAsP), Indium gallium arsenide phosphide (InGaAsP), Aluminium indium arsenide phosphide (AlInAsP), Aluminium gallium arsenide nitride (AlGaAsN), Indium gallium arsenide nitride (InGaAsN), Indium aluminium arsenide nitride (InAlAsN), Gallium arsenide antimonide nitride (GaAsSbN), Gallium indium nitride arsenide antimonide (GaInNAsSb), Gallium indium arsenide antimonide phosphide (GaInAsSbP), Cadmium selenide (CdSe), Cadmium sulfide (CdS), Cadmium telluride (CdTe), Zinc oxide (ZnO), Zinc selenide (ZnSe), Zinc sulfide (ZnS), Zinc telluride (ZnTe), Cadmium zinc telluride (CdZnTe, "CZT"), Mercury cadmium telluride (HgCdTe), Mercury zinc telluride (HgZnTe), Mercury zinc selenide (HgZnSe), Cuprous chloride (CuCl), Lead selenide (PbSe), Lead sulfide (PbS), Lead telluride (PbTe), Tin sulfide (SnS), Tin telluride (SnTe), lead tin telluride (PbSnTe), Thallium tin telluride ($Tl_2SnTe_5$), Thallium germanium telluride ($Tl_2GeTe_5$), Bismuth telluride ($Bi_2Te_3$), Cadmium phosphide ($Cd_3P_2$), Cadmium arsenide ($Cd_3As_2$), Cadmium antimonide ($Cd_3Sb_2$), Zinc phosphide ($Zn_3P_2$), Zinc arsenide ($Zn_3As_2$), Zinc antimonide ($Zn_3Sb_2$), Lead(II) iodide ($PbI_2$), Molybdenum disulfide ($MoS_2$), Gallium selenide (GaSe), Tin sulfide (SnS), Bismuth sulfide ($Bi_2S_3$), Copper indium gallium selenide (CIGS), Platinum silicide (PtSi), Bismuth(III) iodide ($BiI_3$), Mercury(II) iodide ($HgI_2$), Thallium(I) bromide (TlBr), Titanium dioxide: anatase ($TiO_2$), Copper(I) oxide ($Cu_2O$), Copper(II) oxide (CuO), Uranium dioxide ($UO_2$), Uranium trioxide ($UO_3$), and the like. Other suitable materials for QDs of the invention include organic semiconductors comprising pentacene, anthracene and rubrene. Still other suitable materials for QDs of the invention include magnetic semiconductors such as manganese-doped indium arsenide and gallium arsenide, manganese-doped indium antimonide, manganese- and iron-doped indium oxide, manganese doped zinc oxide, and chromium doped aluminum nitride, iron-doped tin dioxide, n-type Cobalt-doped zinc oxide, Cobalt-doped titanium dioxide (both rutile and anatase), Chromium-doped rutile, Iron-doped rutile and iron-doped anatase, Nickel-doped anatase, and Manganese-doped tin dioxide.

Some aspects of the present invention provide methods for stimulating cells using quantum dots. In some embodiments, quantum dots that are responsive to wavelengths of light outside the visible spectrum of light, e.g., in the infrared region of about 750 nm to about 1 mm wavelength are used. Typically, these quantum dots produce a local field charge (i.e., photovoltaic response), a photoluminescent (e.g., emission of light), or a combination of the two when exposed to infrared energy.

While methods of the invention can be used to treat any clinical conditions associated with impaired cell function due to improper or no electrical stimulation, for the sake of brevity and clarity the present invention will now be described for treating vision impairment. However, it should be appreciated that the scope of the invention is not limited to treating vision impairment, but rather includes treating any clinical condition that can be treated using an electrical stimulation of a cell. The terms "treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

Quantum dots for use with the invention can be formed using a variety of techniques. For example, the quantum dots can be formed by creating a region of a first material having a first band gap surrounded by a second material of a second band gap, wherein the second band gap is larger than the first band gap. Exemplary quantum dots produced by such a process include, but are not limited to, a cadmium selenide (CdSe) core surrounded by a zinc selenide (ZnS) shell.

Alternatively, self-assembled quantum dots nucleate spontaneously under certain conditions during molecular beam epitaxy (MBE) and metalorganic vapor phase epitaxy (MOVPE), when a material is grown on a substrate to which it is not lattice matched. The resulting strain between the grown layer and the substrate produces coherently strained islands on top of a two-dimensional "wetting-layer." The islands can be subsequently surrounded by a shell to form the quantum dot.

Individual quantum dots can also be created from two-dimensional electron or hole gases present in remotely doped quantum wells or semiconductor heterostructures. In this case, a surface is coated with a thin layer of photoresist. A lateral pattern is then defined in the resist by electron beam lithography. This pattern can then be transferred to the electron or hole gas by etching, or by depositing metal electrodes (lift-off process) that allow the application of external voltages between the electron gas and the electrodes.

Quantum dots can also be formed in quantum well structures due to monolayer fluctuations in the well's thickness. Alternatively, quantum dots can be produced by Ultrasonic Aerosol Pyrolysis (UAP).

In some embodiments, QDs include an inner semiconductor core formed of, for example, indium/gallium/phosphide, silicon, gallium arsenide, cadmium telluride, copper indium gallium selenide, indium gallium nitride, carbon, colloidal gold, colloidal silver, or organic materials such as polymer-fullerene heterojunctions (e.g., $P3HT+C_{60}$), organic nanocrystal solar cells (e.g., cadmium selenide or cadmium telluride), dye sensitized cells (e.g., dye and titanium oxide or nobelium oxide), or a tandem cell (e.g., copper-phthalocyanin+$C_{60}$); a shell, formed of, for example, zinc selenide or other suitable material; a coating, formed of, for example, PEG lipids or other suitable material; and biofunctional material, formed of, for example, biotin, streptavadin, adhesion proteins, vitamins, organic an inorganic compounds, carbohydrates, aptamers, amino acids, lipids, hyaluronic acid, or other suitable proteins. Such proteins would include, but not limited to, individual amino acids, small peptides, antibodies including human, animal, humanized, monoclonal, and chimeric antibodies used to target various cells and cellular structures, as well as the various classes of antibodies such as IgG, IgM, IgA, IgM, and IgD. The quantum dots could further be conjugated with one another in various combinations, as well as with the proteins, peptides, and amino-acids, and other compounds listed above.

In some embodiments, there are no external components in the quantum dot solution. Instead, the stimulus (i.e., quantum dot) is placed directly at the retinal photoreceptor, the origin of the intricate interplay of neural wiring that forms the basis of vision. Thus, in one particular embodiment, methods of the invention are directed to treating vision impairment (e.g., restoration of visual function) through the implantation of photoactive nanoparticles into the mammalian eye.

As discussed in more detail below, the present inventors have shown the efficacy and utility of infrared photovoltaic nanoparticles implanted into the mammalian eye to sensitize retinal neural tissue to electromagnetic wavelengths outside the visible spectrum of light.

Quantum dots implanted in the eye and exposed to infrared energy emit a localized electric current thereby "jump-starting" retinal photoreceptors and initiating an action potential, thus allowing the subject to "see" infrared energy. All objects emit infrared radiation based on their temperatures, making it possible to "visualize" the surrounding environment without visible illumination.

Figure 1:
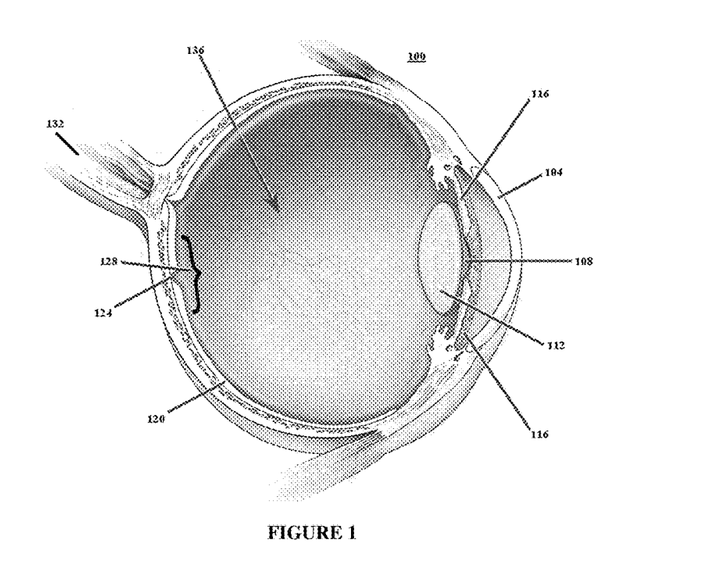
FIG. 1 is a schematic illustration of an eye.

FIG. 1 is a schematic illustration of an eye 100. The eye 100 includes cornea 104, pupil 108, lens 112, iris 116, retina 120, fovea 124, macula 128, optic nerve 132, and vitreous gel 136. Retina 120 is the neural tissue which lines the posterior aspect of the eye 100. When struck by light, retina 120 sends an electrical response through optic nerve 132 to the brain. In some aspects of the invention, photoactive quantum dots responsive to infrared energy are injected into vitreous gel 136 and bind to the retinal photoreceptors, creating a visual response to wavelengths of energy outside the visible spectrum.

Quantum dots can be placed on a surface of retina 120 or in a subretinal or intraretinal area, such as a space located between a Bruch's membrane and outer segments, or directly into the cells themselves. Quantum dots can be placed directly in such locations or they can be coated with a bio-targeted material, which adheres to particular cells, such as ganglia or bipolar cells or photoreceptors. Further, the quantum dots can be internalized by the target cells. The quantum dots fluoresce, emit an electrical potential or current, or a combination thereof, when exposed to infrared radiation. The electrical potential is believed to stimulate rods and cones or other portions of retina such the retinal pigment epithelium, inner nuclear layer, outer nuclear layer, ganglion cell layer, amacrine cells, bipolar cells, Mueller's cells, astryocytes and glial cells. 120. The color of fluorescence and properties of the electrical potential general depend on the shape, size, and materials of the quantum dots. As stated herein, quantum dots can be formed using a variety of techniques. For example, the quantum dots can be formed by creating a region of a first material having a first bandgap surrounded by a second material of a second bandgap, wherein the second badgap is larger than the first bandgap. For example, a quantum dot can include a cadmium selenide (CdSe) core surrounded by a zinc selenide (ZnS) shell.

Alternatively, self-assembled quantum dots nucleate spontaneously under certain conditions during molecular beam epitaxy (MBE) and metallorganic vapor phase epitaxy (MOVPE), when a material is grown on a substrate to which it is not lattice matched. The resulting strain between the grown layer and the substrate produces coherently strained islands on top of a two-dimensional "wetting-layer." The islands can be subsequently surrounded by a shell to form the quantum dot.

Individual quantum dots can also be created from two-dimensional electron or hole gases present in remotely doped quantum wells or semiconductor heterostructures. In this case, a surface is coated with a thin layer of photoresist. A lateral pattern is then defined in the resist by electron beam lithography. This pattern can then be transferred to the electron or hole gas by etching, or by depositing metal electrodes (lift-off process) that allow the application of external voltages between the electron gas and the electrodes.

Quantum dots can also be formed in quantum well structures due to monolayer fluctuations in the well's thickness.

Use of quantum dots is advantageous because inter alia it allows for less invasive methods of implanting the devices, which in turn minimizes trauma and scaring of the tissue. In addition, because the particles are so small, in retina the particles block relatively little light from photoreceptors. Further, the quantum dots can be injected into a wider field of vision, compared to larger devices.

In some instances, these quantum dots are injected intraocularly. Upon exposure to infrared energy, these quantum dots produce a local field charge and stimulate retinal cells, resulting in a visual response to wavelengths of light outside the visible spectrum of light. Such quantum dots can be used for creating endogenous night vision, for example, to aid in visualizing surrounding environment with or without illumination with visible light. All objects emit infrared radiation based on their temperatures, making it possible to "visualize" the surrounding environment without visible illumination.

In other aspects of the invention, QDs in the infrared region (IR-QDs) are used. For example, QDs that are attached to protein or antibody can be used to deliver to target cells such as peripheral neural tissue (peripheral nerves), central neural tissue (CNS: spinal cord, brain), etc. Alternatively, IR-QDs can be injected directly into damaged neural tissues.

IR can penetrate up to 2 inches into human tissues. Thus, in some embodiments, IR-QDs are placed or attached on or near damages tissues that are activated by electrical stimulation. After IR-QDs are placed or attached on or near damages tissues, they are exposed to infrared energy resulting in photovoltaic response, e.g., electrical stimulation of damaged tissues. Such methods can be used for treating or rehabilitating a variety of clinical conditions including, but not limited to, stroke, spinal cord injury, peripheral nerve injury, demylinating disease, such as multiple sclerosis, etc.

In other aspects of the invention generally provide methods for stimulating an electrical response in cells using QDs. The method of the present invention can be used to stimulate any cells that function by electrical stimulation including retina, neurons, etc. QDs can be delivered to or near the target cells using any of the methods known to one skilled in the art including attaching QDs to antibody or protein, as well as by injecting QDs directly to the target site or by placing the QDs via a surgical means either proximal or internal to the cell.

In some embodiments of the invention, a plurality of quantum dots responsive to IR are employed to stimulate cells based on incident IR light. However, it should be appreciated that various other combinations of nanoparticles/quantum dots are also within the scope of the invention.

Use of photoactive nanoparticles such as quantum dots to stimulate electrical response of cells is advantageous in some instances because it allows for less invasive methods of implanting the devices, which in turn minimizes trauma and scaring of the cells.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Animals and Experimental Design

This experiment utilized the Brown-Norway rat, and all procedures were done using animals 4 weeks of age. A total of 20 eyes from 10 rats were used in these experiments. The rats were divided into the following groups: a control group with no intervention and four groups receiving an intravitreal injection of 6 microliters of a colloidal solution of quantum dots responsive to energy in the infrared spectrum. The composition of the quantum dots tested were: indium gallium phosphide (eBioScience, San Diego, Calif.), lead sulfide (Evident Technologies, Troy, N.Y.), cadmium selenium telluride, zinc cadmium (Invitrogen Corp., Carlsbad, Calif.), and colloidal gold (SPI mark, West Chester, Pa.).

Quantum dots can also be prepared as described herein including by Ultrasonic Aerosol Pyrolysis (UAP) method. In this method, the quantum dot size is tuned via variation of the precursor solution concentration or the initial aerosol diameter, which allow control of the quantum dot diameter from a few to tens of nanometers. The absorption properties of this materials system can be tuned through changes in size.

Intravitreal injections were done at the fourth week of life, and the animals were monitored for the subsequent six weeks with serial electroretinography (ERG) recordings. Prior to dosing, the animals were anesthetized using ketamine (80 mg/kg) and xylazine (5-10 mg/kg) anesthesia and the surgical eye were prepped with betadine. The animals were monitored every 4-5 minutes while under anesthesia by observing any response to a toe or skin pinch. A colloidal suspension of the quantum dots was injected into the vitreous via pars plana of the surgical eye of each animal. A Hamilton microinjector was used to deliver a dose of 6 microliters of colloidal quantum dot solution into the vitreous cavity. All procedures were done under direct visualization using a slit-lamp biomicroscope, taking care to avoid injury to the crystalline lens. The animals were monitored daily for the first five days following injection for any signs of infection or alteration in behavior. All the animals were then evaluated 6 weeks post-implantation.

Electroretinogram (ERG) Testing

ERGs were performed weekly to measure the response of the retina to infrared radiation, using a hand held Ganzfeld stimulator, the standard light apparatus for performing electroretinography, equipped with an infrared filter. Both dark- and light-adapted ERGs were recorded at one week intervals. During each recording session, rats were dark-adapted overnight. The animals were placed under ketamine (80 mg/kg)/xylazine (5-10 mg/kg) anesthesia and their pupils dilated (1% tropicamide, 1% cyclopentolate) and cornea anaesthetized (1% proparacaine).

ERGs were recorded from both eyes simultaneously with silver wire electrode loops in contact with the corneal surface through a layer of 1% methylcellulose. Platinum needle electrodes placed in each cheek and the tail served as reference and ground, respectively. Dark-adapted (scotopic) responses were recorded to stimuli presented in order of increasing luminance from $9.5 \times 10^{-4}$ to 137 cd s $m^{-2}$ with the infrared filter in place. Five to ten responses were averaged for each intensity with an interval between stimuli increasing from 15 s to 1 min with brighter stimuli. After 15 minutes of light adaptation, ERG photopic responses to stimuli were recorded in a similar manner.

All stimuli were presented by an LKC Desk-top Ganzfeld large enough to encompass visual fields from both eyes. The responses were filtered from 1 to 1500 Hz with response acquisition and averaging coordinated by an LKC UTAS-E 3000 (Gaithersburg, Md.) signal averaging system.

Electrophysiology Data Analysis

Both a- and b-wave amplitudes were measured. The a-wave was measured from baseline to trough. The b-wave was measured from a-wave trough to peak of the positive b-wave. Amplitude measures were analyzed over post-implantation times across the treatment groups.

Results

Figure 2:
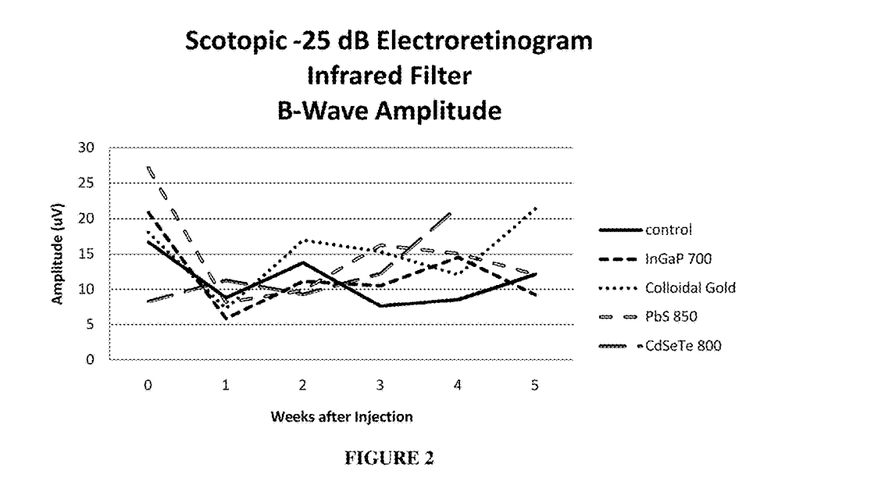
FIG. 2 is a graph of Scotopic dark-adapted ERG in the Brown-Norway rats that received an intraocular injection of infrared quantum dots composed of different materials.

FIG. 2 is a graph of Scotopic dark-adapted ERG, flash stimulus of −25 dB, which elicits predominantly rod photoreceptor response, in the Brown-Norway rat. The standard flash was covered with an infrared filter. The control group had no intervention, and the four other groups had received an intraocular injection of quantum dots composed of materials sensitive to infrared energy. All treatment groups demonstrated a minimum of 30% increase in B-wave amplitude at weeks 3 and 4 post-injection.

Figure 3:
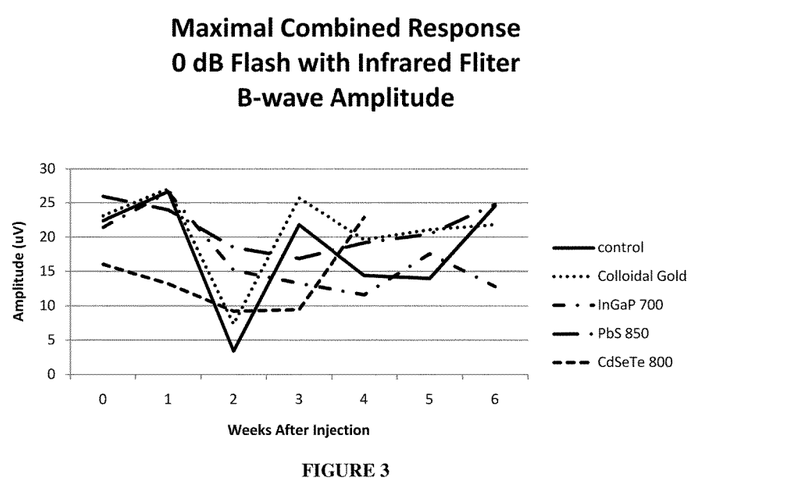
FIG. 3 is a graph of 0 dB Flash ERG in the Brown-Norway rats that received an intraocular injection of different IR quantum dots.

FIG. 3 is a graph of the 0 dB Flash ERG, which elicits both rod and cone photoreceptor response, in the Brown-Norway rat. The standard flash was covered with an infrared filter. The control group had no intervention, and the four other groups had received an intraocular injection of quantum dots composed of materials sensitive to infrared energy. All treatment groups demonstrated an increase of at least 30% at week 2. The colloidal gold and PbS groups had at least a 30% increase at weeks 4 and 5, and this is seen again in the CdSeTe group at week 4.

Figure 4:
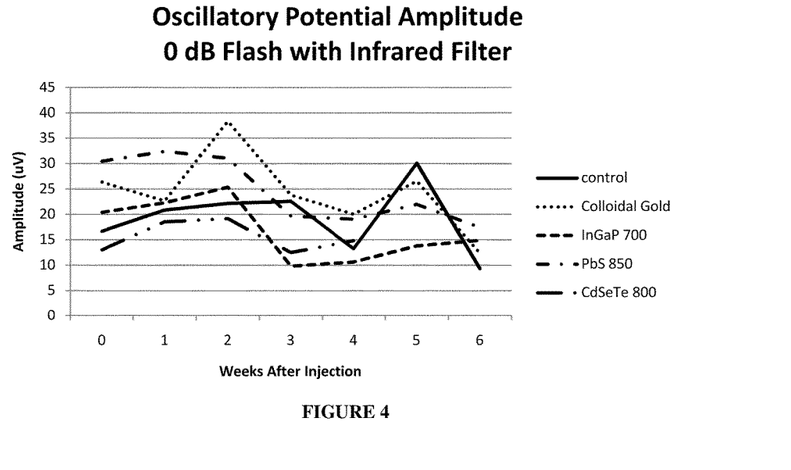
FIG. 4 is a graph of the oscillatory potential recording in the Brown-Norway rats that received an intraocular injection of different IR quantum dots.

FIG. 4 is a graph of the oscillatory potential recording, which measures electrical activity of the inner retina, in the Brown-Norway rat. The standard flash was covered with an infrared filter. The control group had no intervention, and the four other groups had received an intraocular injection of quantum dots composed of materials sensitive to infrared energy. The colloidal group demonstrated an increase of at least 30% over the control group at weeks 2, 4, and 6 post injection. Similarly, the PbS groups demonstrated at least 30% increase over the control group at weeks 1, 2, 4 and 6 post injection. The InGaP groups demonstrated a 59% increase over the control group at week 6.

Figure 5:
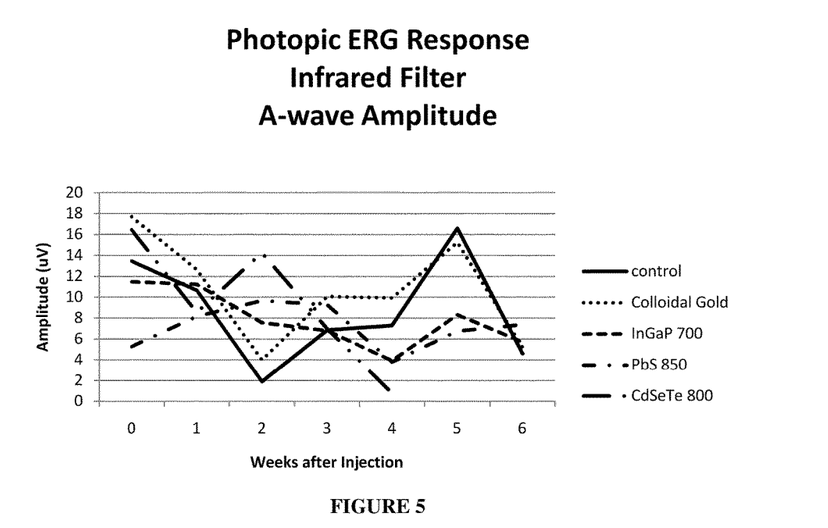
FIG. 5 is a graph of photopic 0 dB ERG recording in the Brown-Norway rats that received an intraocular injection of different IR quantum dots.

FIG. 5 is a graph of a light adapted, photopic 0 dB ERG recording, which elicits predominantly cone photoreceptor response, in the Brown-Norway rat. The standard flash was covered with an infrared filter. The control group had no intervention. The four treatment groups had received intraocular injections of quantum dots composed of materials sensitive to infrared energy. All treatment groups demonstrated a minimum increase in a-wave amplitude of greater than 30% at 2 weeks post injection. For the colloidal gold group this was sustained through weeks 3 and 4, and for the PbS group through week 3.

Figure 6:
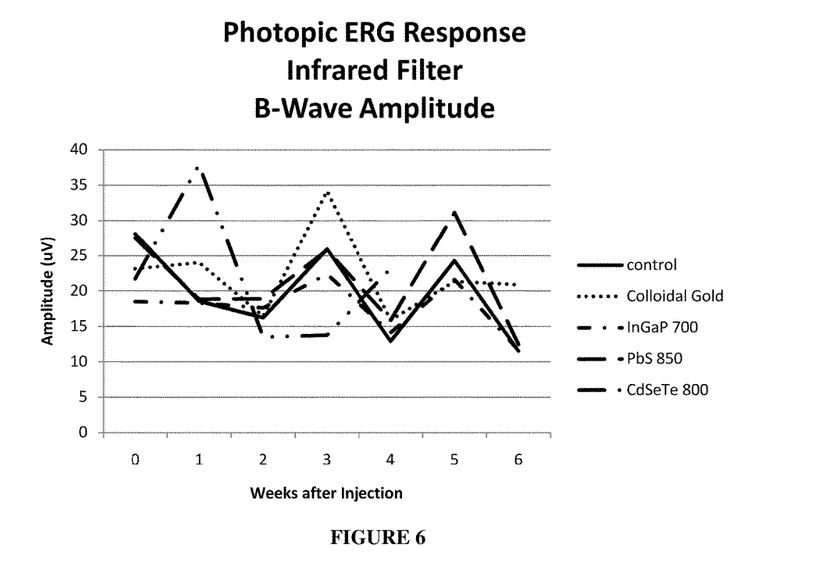
FIG. 6 is a graph of photopic 0 dB ERG recording in the Brown-Norway rats that received an intraocular injection of different IR quantum dots.

FIG. 6 is a graph of a light adapted, photopic 0 dB ERG recording, which elicits predominantly cone photoreceptor response, in the Brown-Norway rat. The standard flash was covered with an infrared filter. The control group had no intervention. The four treatment groups had received intraocular injections of quantum dots composed of materials sensitive to infrared energy. The colloidal gold and CdSeTe groups demonstrated a minimum increase in b-wave amplitude of greater than 30% at 1 week post injection. For the colloidal gold group, a greater than 30% increase over the control groups occurred again at weeks 3 and 6, and for the CdSeTe group at week 4.

Similarly, quantum dots can be placed (e.g., via surgery, injection, or any other methods known to one skilled in the art) proximal or internal to appropriate neurons to treat other neurological disorders using infrared radiation. For example, in the case of spinal cord injury, the infrared QD would be injected via a transcutaneous needle to an area proximal to the site of injury, and then the site exposed to infrared energy to stimulate the quantum dots and in turn electrically stimulate the neural tissue. This could include the axons of the neurons themselves, or the proximal supporting glial tissue. Further, the quantum dots can be injected proximal or internal to the targeted cells. Similarly, for cases of peripheral nerve injury, the site of injury is accessed either surgically or by ultrasound guided needle injection and the quantum dots placed in contact with the injured tissue, which is then irradiated with infrared injury to stimulate the quantum dots and in turn the damaged tissue. Alternatively, tissue impregnated with quantum dots in vitro could then be placed surgically in vivo into the area of injury to create the similar effect. For example, cultured retinal pigment epithelial cells can be impregnated with quantum dots, and these treated cells can then be placed surgically beneath the retina.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for providing a subject with endogenous night vision, the method comprising:
   providing a quantum dot to the subject not experiencing or displaying symptoms of visual impairment, wherein the subject comprises a retina and the retina comprises a retinal cell;
   wherein the quantum dot emits a local field charge in response to exclusively infrared radiation emitted by an object and not in response to wavelengths of light within the visible spectrum of light;
   providing a bio-targeted material to localize the quantum dot proximal to the retinal cell; and exposing the retina to infrared radiation, wherein the local field charge emitted by the quantum dot results in an action potential;

wherein the action potential results in a visual response; and wherein the visual response provides the subject with endogenous night vision, allowing the subject comprising the retina to visualize the object in an environment without visible illumination.

2. The method of claim 1, wherein the quantum dot is coated with the bio-targeted material.

3. The method of claim 2, wherein the bio-targeted material is biotin or streptavadin.

4. The method of claim 1, wherein the quantum dot is not photoluminescent.

* * * * *